United States Patent [19]

Strong-Gunderson et al.

[11] Patent Number: 5,807,697
[45] Date of Patent: Sep. 15, 1998

[54] BIOLOGICAL TRACER METHOD

[75] Inventors: Janet M. Strong-Gunderson, Ten Mile; Anthony V. Palumbo, Oak Ridge, both of Tenn.

[73] Assignee: Lockheed Martin Energy Systems, Inc., Oak Ridge, Tenn.

[21] Appl. No.: 639,234

[22] Filed: Apr. 19, 1996

[51] Int. Cl.$^6$ ............................... C12Q 1/02; C12Q 1/00; C12N 1/00; C12N 1/20

[52] U.S. Cl. ................................. 435/29; 435/4; 435/847; 435/874; 435/876; 435/252.34; 435/253.2; 239/1; 239/2.1; 239/2.2; 239/14.2; 239/9; 239/10; 424/93.47

[58] Field of Search ................................. 435/29, 4, 847, 435/874, 876, 252.34, 253.2; 239/1, 2.1, 2.2, 14.2, 9, 10; 424/93.47

[56] References Cited

U.S. PATENT DOCUMENTS

| | | | |
|---|---|---|---|
| 4,464,473 | 8/1984 | Orser et al. | 435/172.3 |
| 4,706,473 | 11/1987 | Lindsey | 62/64 |
| 4,784,943 | 11/1988 | Warren et al. | 435/29 |
| 4,796,805 | 1/1989 | Carlberg et al. | 435/29 |
| 5,489,521 | 2/1996 | So et al. | 435/29 |

OTHER PUBLICATIONS

"Concepts and Methods for Assessing Solute Dyamics in Stream Ecosystems," Stream Solute Workshop, the University of Missippi, Feb. 1–5, 1989, *J. N. Am. Benthol. Soc.*, 1990, 9(2):95–119.

R. A. Goodnow et al "Fate of Ice Nucleation–Active *Pseudomanas syringae* Strains in Alpine Soils and Waters and in Synthetic Snow Samples," *App. & Environmental Microbiology*, Jul. 1990, pp. 2223–2227.

P. M. Wallis et al "Effects of Using Ice Nucleating Bacteria (Snomax) on Snow, Vegetation and Soil at Mount St. Louis, Ontario Canada," Hyperion Research Ltd. Report, May 12, 1989.

G. Vali, "Principles of Ice Nucleation," Chapter 1, *Biological Ice Nucleation and Its Applications*, APS Press, pp. 1–28, 1995.

G. Vali, "Quantitative Evaluation of Experimental Results on the Heterogeneous Freezing Nucleation of Supercooled Liquids," *J. Atmos. Sci.*, V. 28, pp. 402–409, 1971. (No copy available –will be sent in later).

*Primary Examiner*—Louise N. Leary
*Attorney, Agent, or Firm*—Shelley L. Stafford

[57] ABSTRACT

The present invention is a biological tracer method for characterizing the movement of a material through a medium, comprising the steps of: introducing a biological tracer comprising a microorganism having ice nucleating activity into a medium; collecting at least one sample of the medium from a point removed from the introduction point; and analyzing the sample for the presence of the biological tracer. The present invention is also a method for using a biological tracer as a label for material identification by introducing a biological tracer having ice nucleating activity into a material, collecting a sample of a portion of the labelled material and analyzing the sample for the presence of the biological tracer.

13 Claims, 2 Drawing Sheets

BIOLOGICAL TRACER METHOD

This invention was made with Government support under contract DE-AC05-840R21400 awarded by the U.S. Department of Energy to Lockheed Martin Energy Systems, Inc., and the Government has certain rights in this invention.

FIELD OF THE INVENTION

The present invention relates to a tracing method and more particularly to a biological tracer method for characterizing the movement of a material through a medium and for using the biological tracer as a label for material identification.

BACKGROUND OF THE INVENTION

The remediation of hazardous waste sites requires detailed site characterization. For example, in surface and groundwater remediation, characterizing the flow paths and velocity is a major objective. In addition, it is important to characterize the transport of contaminants, colloidal particles, bacteria and nutrients in groundwater, as well as in other types of remediation sites, such as drilling muds, and streams.

Conventional tracer techniques used for these purposes include dissolved solutes, microsphere beads, dyes, gases, and radioactive tracers. These methods, however, have several limitations. Radioactive tracers have obvious regulatory problems associated with deliberate release of radioactive material. In addition, this method requires sophisticated equipment for sample analysis, and the half-life of the tracer may be too long or too short for practical use. Microsphere beads are limited because they are nonbiodegradable. Their assay is labor intensive. They are time consuming and difficult to count and their persistence may preclude similar studies at the site. Solutes such as NaCl identify solute transport, but do not mimic microbial and colloid transport, which is essential to characterize for effective in-situ remediation. Gas tracer methods do not have the same penetration characteristics as bacteria; they are more difficult to sample and detect, and are likely to give false positives for sample integrity. Common dye tracers (rhodamine, eosine, fluorosine etc.) are not readily biodegradable and may remain several years after their use, therefore precluding use (W. Sanford et al. Personal Communication) more than once within a given region/site.

Accordingly, a need in the art exists for a tracer method which is easy to use, give rapid results, biodegradable, and highly sensitive.

OBJECTS OF THE INVENTION

It is an object of the invention to provide a new tracer method for characterizing the movement of a material through a medium.

It is another object of the invention to provide a new tracer method for characterizing the movement of a material through a medium that is easy to use.

It is a further object of the invention to provide a new tracer method for characterizing the movement of a material through a medium that gives rapid results.

It is yet another object of the invention to provide a new tracer method for characterizing the movement of a material through a medium that is biodegradable.

It is still yet another object of the invention to provide a new tracer method for characterizing the movement of a material through a medium that is highly sensitive.

It is another object of the invention to provide a new tracer method using a biological tracer as a label for material identification.

It is yet another object of the invention to provide a new tracer method using a biological tracer as a label for material identification that is easy to use.

It is a further object of the invention to provide a new tracer method using a biological tracer as a label for material identification that gives rapid results.

It is still yet another object of the invention to provide a new tracer method using a biological tracer as a label for material identification that is biodegradable.

It is a further object of the invention to provide a new tracer method using a biological tracer as a label for material identification that is highly sensitive.

Further and other objects of the present invention will become apparent from the description contained herein.

SUMMARY

In accordance with one aspect of the invention, the present invention is a biological tracer method for characterizing the movement of a material through a medium, comprising the steps of introducing a biological tracer comprising a microorganism having ice nucleating activity into a medium; collecting at least one sample of the medium from a point removed from the introduction point; and analyzing the at least one sample for the presence of the biological tracer.

In accordance with another aspect of the invention, the present invention is a method for using a biological tracer as a label for material identification, comprising the steps of introducing into a material a biological tracer comprising a microorganism having ice nucleating activity; collecting at least one sample of a portion of said labelled material removed from the introduction point; and analyzing the sample for the presence of the biological tracer.

DETAILED DESCRIPTION OF THE INVENTION

Figure 1:
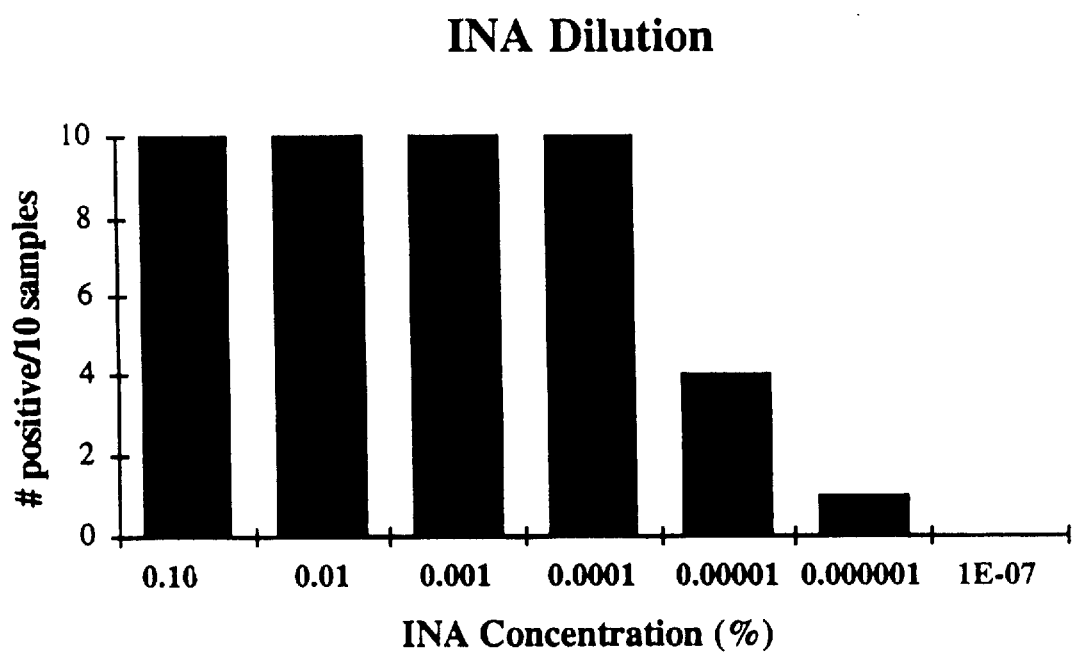

Applicant's invention is an inexpensive, sensitive, easy-to detect (in real time), method using a biological tracer for environmental tracing. As a tracer it can be used for hazardous waste site characterization, the evaluation of stream flow dynamics, analyzing surface water and groundwater flows, and contaminant transport, tracing of drilling fluid, microbial transport through the subsurface, etc. The tracer is formed of an aqueous suspension of an ice nucleating active bacteria such as *Pseudomonas syringae, P. fluorescens, Erwinia herbicola*, etc. Ice nucleating microorganisms were identified in the early 1970's. Ice nucleating microorganisms synthesize large, outer membrane proteins which aggregate within the membrane and function as a template for the formation of small ice crystal seeds called "ice nuclei". As a result, these microorganisms having ice nucleating activity (INA) are unique in their potent ability to catalyze ice nucleation at temperatures as high as −2° C., wherein under similar and specific assay conditions, water does not freeze until −15° C. and ground waters do not freeze until about −10° C. Thus, at high subzero temperatures (−2° to −5° C.), water will supercool and remain as a liquid. Therefore, if INA bacteria are present in a ground water sample, ice crystallization will occur at these high subzero temperatures. This unique ice nucleating phenomena is the key to using the INA bacteria as an innovative environmental tracer.

This ice nucleating activity is still retained by microorganisms killed by radiation or antibiotics. In addition, the genes responsible for INA have been isolated and partially sequenced. Ice nucleating microorganisms have been utilized in several commercial areas, including snowmaking, biological pest control and atmospheric precipitation processes. However, the use of ice nucleating microorganisms as used in the method of the present invention is not known in the art.

A typical microorganism that is useful in the method of the present invention as a biological tracer is a Pseudomonad, and particularly *Pseudomonas syringae*. One embodiment of the present invention uses the commercially available Snomax® product (available from Snomax Technologies, Rochester, N.Y.), which is the ice nucleating microorganism, *Pseudomonas syringae*, that has been processed (killed and mixed with an inert ingredient). Any species or any microorganism having ice nucleating activity may be used as a biological tracer in the present invention. The ice nucleating microorganisms as used in the present invention may be viable or killed, depending on the desired application as described below.

The method of the present invention involves using the biological tracer to characterize the movement of a material through a medium. As used in the present invention, the term "material" includes, but is not limited to, solutes, contaminants, microorganisms, nutrients, chemicals, drilling material (muds, fluids, and gases) in environmental sampling, aqueous solutions, and nonaqueous solutions. The term medium, as used in the present invention, includes, but is not limited to fluid mediums, such as groundwaters (shallow or deep aquifers), surface waters (streams), drilling fluids, and also non-fluid mediums, such as air and other gases, drilling muds, clay matrices, shale matrices, karst matrices, sand matrices and mixtures thereof. The tracer is the dead or alive bacterium *Pseudomonas syringae* and is assayed using freezing-point determination. The tracer can be detected in waters at about $10^{-10}$ mg/L and can be detected in a soil slurry at about $10^{-6}$ mg/kg soil. The tracer can persist for approximately 7–90 days, has been detected for up to 1 year, depending on environmental conditions and concentrations used and is stable at pH 2.3 to 11.0. The presence of organic contaminants, such as toluene, xylene, carbon tetrachloride, and trichloroethylene ($\leq$10 ppm), does not interfere with the tracer assay. In fractured shale, the colloidal tracer was transported at a rate of about 40 meters/day, which is more than two orders of magnitude faster than the estimated transport velocity measured by conventional tracers. The rate indicates that a small volume of the water was moving faster than previously estimated. The INA tracer can also be used as a drilling mud tracer, with results similar to those obtained when using fluorescent microspheres. However, the INA tracer is much more sensitive, having three orders of magnitude greater detection limits and the detection assay is more efficient.

The method of the present invention also involves using the biological tracer as a marker or label for identifying labelled materials. As used in the present invention, the term "material" includes, but is not limited to, solutes, contaminants, microorganisms, nutrients, chemicals, drilling fluid, gas matrices, liquid matrices and solid matrices. The tracer is the alive or dead bacterium having ice nucleating activity and is assayed using freezing-point determination. When the tracer is added to or incorporated into a material, it will provide a "signature" (ice nucleation) that can be assayed. If a material is labeled with the ice nucleating tracer, the assay is used to prove that a material did or did not come from a specific source. The assay of the present invention can be used to detect unlicensed or unauthorized use of a labeled material or for other purposes where identification of a material is needed. The tracer method of the present invention can also be used to identify a material based on the material's ability to incorporate the ice nucleating tracer. For example, ice nucleating activity can be added to a material such as gas or liquid to test the efficiency of a gas or liquid filter. Due to the size range of the tracer microorganism, the method of the present invention can be used as a tracer for a virus, therefore it can be used to test a filter for the ability to exclude a virus.

Assay conditions are simple and based on the observation of the freezing behavior of 10 ul solution volumes. Under specific assay conditions (−5° to −7° C.) these drops freeze only if the tracer is present. The results are available within 3 minutes of sample collection, thus providing a real-time measure. The tracer detection limits are about ng/L, it is stable over a pH range of about 2–11, and maintains its high activity in the presence of a variety of contaminant compounds.

INA bacteria are very specific for ice nucleation and there are few potential interferences from other nucleators. Compounds such as silver iodide (used in cloud seeding) are not active until temperatures fall below about −5° C. Although there are some very unique classes of steroids that can also nucleate water at high subzero temperatures, the only common nucleator that will function at −2° C. is ice itself. The laboratory experiments described below were in direct support of a field test where the INA bacteria were used in combination with other solutes and colloidal tracers to measure ground water velocities in a fractured matrix.

EXAMPLE 1

The INA bacteria was a commercially available, concentrated, freeze-dried and killed preparation of *P. syringae* (Snomax Technologies, Rochester, N.Y.). The material was hydrated in distilled water as a 0.5–1 weight percent solution which corresponded to ca. 5000–10,000 ppm. The tracer concentration and detection limits were calculated from standard curves. A 1000 ppm (weight/volume) solution of tracer was dissolved in sterile water and the ice nucleating activity of the solutions measured using the drop freezing assay as described by G. Vali in the *Journal of Atmospheric Science* volume 28, pages 402–409 in 1971, hereby incorporated by reference. Briefly, this assay consisted of placing approximately ten, 10 ul solution drops on an aluminum weigh boat. The weigh boat floated on the surface of a glycol cooled bath set at −7° C. which corresponded to a drop temperature of about −5° C. at the surface of the aluminum boat. The drops (typically 10 drops/dilution) were observed for 3 minutes and all frozen drops were counted and recorded as the number positive/total drops. These results were compared to the negative controls (tap water or upgradient ground water). Serial dilutions were performed and ice nucleation activity measured to determine the detection limit.

EXAMPLE 2

The short-term stability of the INA tracer was measured in the presence of several common ground water contaminants. The initial INA concentration was approximately 100 ppm in a contaminant solution containing 1 ppm of the following: toluene, naphthalene, xylenes, carbon tetrachloride, methylene chloride or trichloroethylene. Since the contaminants tested were volatile, a modification of the tube freezing assay (described by G. Vali in 1995 entitled, "Principles of Ice Nucleation", chapter 1, *Biological Ice*

*Nucleation and Its Applications*, APS Press, pages 1–28, hereby incorporated by reference) was performed with a 100 ul test solution in an eppendorf microcentrifuge tube. The samples were capped and suspended in the low temperature bath of −7° C. and observed 3 minutes for ice nucleation. Samples were run in triplicate and compared to the negative controls of water and water/contaminant mixture.

An INA tracer concentration (10 ppm) was assayed for stability over a wide Ph range. The Ph was adjusted using a strong acid or base in incremental steps of 0.5 pH units from an initial value of 7 down to 2.0 and from 7 up to 11.0. The drop freezing assay was performed to qualitatively determine ice nucleating activity throughout the ranges (n=11 pH intervals).

Soil samples are hydrated at a ration of 1:1, if possible. Subsequent changes in this ration depends upon soil characterization. Soil samples are vortexed and allowed to settle for approximately 1 minute. The aqueous phase is analyzed for the presence of the tracer using the method described above.

EXAMPLE 3

The transport characteristics of the INA tracer were tested in a small soil column. Rich organic soil primarily composed of A-horizon material (Walker Branch Watershed, Oak Ridge National Laboratory, Oak Ridge, Tenn.) was used to fill a 30 mL column and flushed with sterile water. The void volume was estimated to be about 5 mL. The column was initially flushed with sterile water and subsequently 100 uL of the tracer solution (100 ppm INA in 85% NaCl) was dispensed onto the top of the column. The column was flushed with distilled water and 1 mL fractions were collected. The NaCl concentration was measured using a Waters HPLC. Solution samples were filtered with a 3mm, 0.45 um Acrodisc 3 CR PTFE. A 20 uL sample injection loop and an IC-Pak In Exclusion 7.8 mm×15 cm column were used for the NaCl analysis. Total conductivity was measured with a Waters Conductivity Detector, model 430. The ice nucleating activity was measured on the low temperature bath using the drop freezing assay as previously described.

These laboratory experiments support the use of INA bacteria as a quick and inexpensive tracer for a variety of environmental conditions. This tracer fulfills a need for a product that simulates not only colloid transport but bacterial transport which is critical to in situ bioremediation activities.

The detection limits for the INA tracer using the drop freezing assay was determined to be 0.0000001% or 0.0001 ppm, see FIG. 1. In theory, the INA tracer has a detection limit of 1 bacterium or nucleation site per sample volume. Thus, the detection limit should be even lower in the 100 uL tube assay used in the stability assays previously described. Once ice crystal growth has been initiated, i.e. nucleation has occurred, crystal propagation occurs throughout the sample. This low detection limit is important to large scale characterization studies where in situ dilution factors may be subject to gross underestimation or unknown. This low detection limit allows for the determination of breakthrough over a wider range of dilution than for many other tracers.

In addition to being very sensitive, the sample analysis is very rapid. Qualitative results can be obtained within 3 minutes of sample collection, thus providing real-time answers. Quick response times are important during dynamic field operations such as forced bacterial injection in bioremediation activities, pump and treat, etc., and to decide when to sample for other injected materials.

Site characterization activities that require repeated investigation will benefit from the use of the present invention using this biodegradable tracer. Changes in ground water flow velocities and flow paths may differ from wet to dry seasons, or may be impacted by remediation activities such as pump and treat, etc. The ability to use the same tracer under a variety of conditions provides continuity in data interpretation. Room temperature experiments have shown that within 4–8 weeks the tracer activity begins to decrease. The overall nucleation decrease is dependent on temperature and natural microbial populations which utilize the INA tracer (*P. syrinaae*) as a food source.

Currently there is a significant amount of labile carbon in the commercially available product that can be metabolized by the natural microbial populations. Thus, it is imperative that care be taken to avoid well plugging and other problems when this product is used in the field. Modifications of the product to increase its suitability as a general environmental tracer are ongoing.

The optimal tracer for hazardous waste site characterization needs to be easy, quick, economical and cannot be affected by the presence of organic and inorganic contaminant compounds. High background levels of solutes and contaminants can impact the detection limits of many typical solute tracers such as dyes, bromide, sodium chloride, etc. Under these conditions, the initial tracer loading/injection concentration could necessitate very high levels which could negatively impact the system under investigation. The addition of several contaminants at 1 ppm (see Table 1) did not interfere with the INA drop freezing assay when performed within 12 hours of tracer contaminant experiments. Since contaminants do not interfere with the assay, the INA tracer can be used at low concentrations. On-going experiments are evaluating the long-term stability (months/years) of the INA tracer under a variety of simulated field conditions and ground water chemistries.

TABLE 1

| Solution Makeup | Contaminant 1 ppm | 100 uL Samples at −5° C. |
|---|---|---|
| water unfrozen | | |
| water + INA | | frozen |
| water + INA | toluene | frozen |
| water + INA | naphthalene | frozen |
| water + INA | xylenes | frozen |
| water + INA | carbon tetrachloride | frozen |
| water + INA | methylene chloride | frozen |
| water + INA | TCE | frozen |
| water + contaminant | tested individually | unfrozen |

The INA tracer was stable over a pH range of 2.3 to 11.0. Thus, its application can be extended from pristine and organic contaminated sites to low pH sites such as acid mine drainage regions. Typically the pH of these types of site characterizations range from a pH of 2–4 and few tracers are known that are stable under these extreme conditions.

Figure 2:
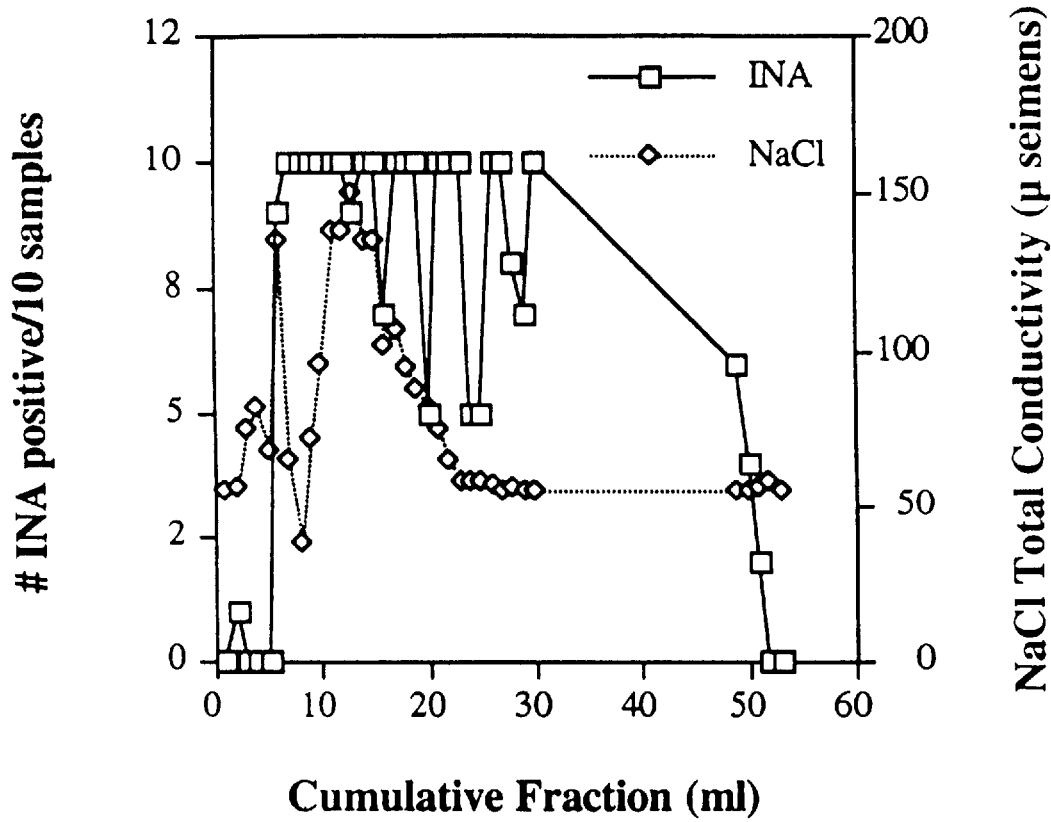

To establish the transport characteristics of the colloidal tracer, both NaCl and INA were flushed as a mixed solution through a soil column. One mL aliquots were assayed and both INA and NaCl. Analysis of the INA/NaCl data show an initial breakthrough at 1 and 3 mL, respectively, while the peak breakthrough occurred at 6 mL (see FIG. 2). The similar transport of the solute and colloid is common in a nonreactive and homogeneous matrix. The effect of matrix diffusion between the tracers and soil appear to be minimal. In a fractured system, the colloid tracer can elute ahead of a soluble tracer. At the end of the experiment, the NaCl tracer returned to the baseline value after 25 mL was eluted, while the INA tracer did not return to baseline until >50 mL. This increased persistence of the INA tracer is due in part to the lower detection limits. There was little to no additional tailing observed for the INA tracer.

The method of the present invention comprises introducing or injecting the INA bacteria into the system that is to be monitored through standard field methods such as, but not limited to, manual addition into well or surface water, constant flow or pulse flow introduction, addition into drilling fluids via sterile bags, etc. Then collecting samples of the medium or the labelled material at various collection points. Techniques for collecting samples use standard field methods such as, but not limited to, manual or autosamplers, dedicated well pumps, down-hole sensors, etc. Then analyzing the collected samples in order to monitor or characterize the movement of the bacteria or in order to identify the presence of the INA bacteria in the labelled material. Transport is followed by determining the freezing point of the samples and comparing it to the freezing point of the background medium. The increase in the mediums's freezing point (about −3° to −5° C.) is the signature of the presence of the INA bacteria and can only be accomplished effectively by the addition of this type of INA product. Thus, if the medium sample freezes at temperatures above −8° C., then it is known the INA tracer has made it to that point in the medium where sampling occurred.

While there has been described what are at present considered the preferred embodiments of the invention, it will be obvious to those skilled in the art that various changes and modifications can be made therein, without departing from the scope of the invention defined by the appended claims.

What is claimed is:

1. A method for using a biological tracer for characterizing the movement of a material through groundwaters, surface waters, drilling fluids, drilling muds, clay matrices, shale matrices, karst matrices, sand matrices and mixtures thereof containing the steps of:
   a) obtaining freezing point temperature of a medium;
   b) introducing at an introduction point in said medium a biological tracer into said medium, said biological tracer comprising a microorganism having ice nucleating activity;
   c) collecting at least one sample of said medium from a point removed from said introduction point;
   d) determining the freezing point of said at least one sample; and
   e) comparing said freezing point of said at least one sample with said freezing point of said medium prior to said introduction of said biological tracer into said medium to characterize said movement of said material through said medium.

2. The method of claim 1 wherein said microorganism comprises at least a portion of said microorganism that retains said ice nucleating activity.

3. The method of claim 1 wherein said microorganism having ice nucleating activity comprises *Pseudomonas syringae, Pseudomonas fluorescens* and *Erwinia herbicola.*

4. The method of claim 1 wherein said biological tracer is introduced into said medium as an aqueous suspension formed of said microorganism having ice nucleating activity.

5. The method of claim 1 wherein said biological tracer is introduced into said medium as a powder.

6. The method of claim 1 wherein said material comprises air, solutes, contaminants, microorganisms, chemicals, drilling fluids, aqueous solutions, nonaqueous solutions and solids.

7. The method of claim 1 wherein said medium comprises fluid mediums and non-fluid mediums.

8. The method of claim 7 wherein said fluid mediums comprise groundwaters, surface waters and drilling fluids.

9. The method of claim 7 wherein said non-fluid mediums comprise air, drilling muds, clay matrices, shale matrices, karst matrices, sand matrices and mixtures thereof.

10. A method for using a biological tracer as a label for material identification, comprising the steps of:
    a) obtaining a freezing point temperature of a material;
    b) introducing into said material at an introduction point of said material a biological tracer as a powder, said biological tracer comprising a microorganism having ice nucleating activity, thereby producing a labelled material;
    c) collecting at least one sample of a portion of said labelled material removed from said introduction point;
    d) determining the freezing point of said at least one sample; and
    e) comparing said freezing point of said at least one sample with said freezing point of said material prior to said introduction of said biological tracer into said material for material identification.

11. The method of claim 1 wherein said microorganism comprises at least a portion of said microorganism that retains said ice nucleating activity.

12. The method of claim 10 wherein said microorganism having ice nucleating activity comprises *Pseudomonas syringae, Pseudomonas fluorescens* and *Erwinia herbicola.*

13. The method of claim 10 wherein said material comprises air, solutes, contaminants, microorganisms, chemicals, drilling fluid, gas matrices, liquid matrices and solid matrices.

* * * * *